US010773095B2

(12) United States Patent
Drake et al.

(10) Patent No.: US 10,773,095 B2
(45) Date of Patent: Sep. 15, 2020

(54) DIRECT MAGNETIC IMAGING WITH METAMATERIAL FOR FOCUSING AND THERMAL ABLATION USING SPION NANOPARTICLES FOR CANCER DIAGNOSIS AND TREATMENT

(75) Inventors: Christina Drake, Oviedo, FL (US); Clara Baleine, Orlando, FL (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 1450 days.

(21) Appl. No.: 14/007,179

(22) PCT Filed: Jun. 21, 2012

(86) PCT No.: PCT/US2012/043547
§ 371 (c)(1),
(2), (4) Date: Sep. 8, 2014

(87) PCT Pub. No.: WO2012/177875
PCT Pub. Date: Dec. 27, 2012

(65) Prior Publication Data
US 2014/0378818 A1  Dec. 25, 2014

Related U.S. Application Data

(60) Provisional application No. 61/499,644, filed on Jun. 21, 2011, provisional application No. 61/513,903, filed on Aug. 1, 2011.

(51) Int. Cl.
*A61B 5/055* (2006.01)
*A61N 2/02* (2006.01)
(Continued)

(52) U.S. Cl.
CPC ............... *A61N 2/02* (2013.01); *A61B 5/055* (2013.01); *A61B 18/04* (2013.01); *A61B 90/39* (2016.02)

(58) Field of Classification Search
CPC .................. H01Q 15/0086; C08L 2203/02
See application file for complete search history.

(56) References Cited

U.S. PATENT DOCUMENTS 5,129,595 A    7/1992  Thiede et al.
5,654,549 A    8/1997  Landecker et al.
(Continued)

FOREIGN PATENT DOCUMENTS

EP    2458396    5/2012
ES    2344391    8/2010
(Continued)

OTHER PUBLICATIONS

Rennings et al "A CRLH Metamaterial based RF Coil Element for Magnetic Resonance Imaging at 7 Tesla" Antennas and Propagation, 2009. EuCAP 2009. 3rd European Conference).*
(Continued)

*Primary Examiner* — Serkan Akar
(74) *Attorney, Agent, or Firm* — Terry M. Sanks, Esq.; Beusse Sanks, PLLC

(57) ABSTRACT

Devices and methods for identifying and destroying cancer cells are disclosed. Devices and methods may relate to techniques of imaging and/or irradiating cells bearing a plurality of surface-modified superparamagnetic iron oxide nanoparticles (SPIONs) therein. Imaging can be realized with a magnetic imaging device that generates an imaging magnetic field. A magnetic field associated with the SPION-bearing cancer cells and resulting from imaging, can be detected with a detection device. Irradiation can be realized with a magnetic field emission device that generates an irradiation magnetic field such that the SPIONs in the SPION-bearing cells are heated as a result of said magnetic field, thereby killing the SPION-bearing cells. The magnetic imaging device may be used as the magnetic field emission device. The magnetic fields produced for imaging and/or
(Continued)

irradiating, as well as the associated magnetic field, can be focused using one or more magnetic metalens devices.

13 Claims, 12 Drawing Sheets

(51) Int. Cl.
*A61B 18/04* (2006.01)
*A61B 90/00* (2016.01)

(56) References Cited

U.S. PATENT DOCUMENTS

| | | | |
|---|---|---|---|
| 5,663,825 | A | 9/1997 | Amon et al. |
| 5,826,178 | A | 10/1998 | Owen |
| 6,326,783 | B1 | 12/2001 | Tanaka |
| 6,493,551 | B1 | 12/2002 | Wang et al. |
| 6,795,037 | B2 | 9/2004 | Greim |
| 6,806,710 | B1 | 10/2004 | Renz et al. |
| 6,927,528 | B2 | 8/2005 | Barillot et al. |
| 6,985,118 | B2 | 1/2006 | Zarro et al. |
| 7,242,364 | B2 | 7/2007 | Ranta |
| 7,345,475 | B2 | 3/2008 | Takeuchi et al. |
| 7,365,701 | B2 | 4/2008 | Werner et al. |
| 7,501,823 | B2 | 3/2009 | Nistler et al. |
| 7,532,008 | B2 | 5/2009 | Pendry et al. |
| 7,623,745 | B2 | 11/2009 | Podolskiy et al. |
| 7,626,392 | B2 | 12/2009 | Nistler et al. |
| 7,688,070 | B2 | 3/2010 | Weyers et al. |
| 7,710,336 | B2 | 5/2010 | Schweizer et al. |
| 7,760,965 | B2 | 7/2010 | Tener et al. |
| 7,808,722 | B2 | 10/2010 | Tonucci |
| 7,864,394 | B1 | 1/2011 | Rule et al. |
| 8,014,062 | B2 | 9/2011 | Scott et al. |
| 8,212,880 | B2 | 7/2012 | Anderson et al. |
| 8,428,385 | B2 | 4/2013 | Whiteside et al. |
| 8,823,848 | B2 | 9/2014 | Chipman et al. |
| 9,194,750 | B2 | 11/2015 | Oster et al. |
| 9,235,876 | B2 | 1/2016 | Hogasten et al. |
| 2004/0244625 | A1 | 12/2004 | Tiernan et al. |
| 2005/0033154 | A1 | 2/2005 | deCharms |
| 2006/0142749 | A1* | 6/2006 | Ivkov ............... A61K 41/0052 606/27 |
| 2006/0255275 | A1 | 11/2006 | Garman et al. |
| 2007/0200566 | A1 | 8/2007 | Clark et al. |
| 2008/0165079 | A1 | 7/2008 | Smith et al. |
| 2008/0192331 | A1* | 8/2008 | Wang ..................... B82Y 20/00 359/315 |
| 2009/0040131 | A1 | 2/2009 | Mosallaei |
| 2009/0096545 | A1 | 4/2009 | O'Hara et al. |
| 2009/0099623 | A1 | 4/2009 | Bentwich |
| 2009/0140946 | A1 | 6/2009 | Ziolkowski et al. |
| 2009/0156976 | A1 | 6/2009 | Korbling et al. |
| 2009/0201221 | A1 | 8/2009 | Werner et al. |
| 2009/0224962 | A1 | 9/2009 | Pao et al. |
| 2009/0284644 | A1 | 11/2009 | McKaughan et al. |
| 2010/0003197 | A1 | 1/2010 | Bikram |
| 2010/0039111 | A1* | 2/2010 | Luekeke ............... G01R 33/341 324/318 |
| 2010/0046853 | A1 | 2/2010 | Goodnough et al. |
| 2010/0047180 | A1* | 2/2010 | Zeng ..................... A61K 33/26 424/9.32 |
| 2010/0000970 | A1 | 4/2010 | Werner et al. |
| 2010/0133488 | A1 | 6/2010 | Giakos |
| 2010/0239504 | A1 | 9/2010 | Liu et al. |
| 2010/0259345 | A1 | 10/2010 | Kim et al. |
| 2011/0074425 | A1 | 3/2011 | Chu et al. |
| 2011/0077506 | A1* | 3/2011 | Driehuys ............... A61K 49/00 600/420 |
| 2011/0204891 | A1 | 8/2011 | Drake et al. |
| 2011/0209110 | A1 | 8/2011 | Grbic et al. |
| 2011/0267244 | A1 | 11/2011 | Rajgopal et al. |
| 2011/0279681 | A1 | 11/2011 | Cabib et al. |
| 2011/0287218 | A1 | 11/2011 | Narimanov |
| 2012/0081511 | A1 | 4/2012 | Kasunic et al. |
| 2012/0082441 | A1 | 4/2012 | Krueger |
| 2012/0105061 | A1 | 5/2012 | Drake et al. |
| 2012/0105267 | A1 | 5/2012 | DeLia et al. |
| 2012/0211665 | A1 | 8/2012 | Cloud et al. |
| 2012/0228563 | A1 | 9/2012 | Fuller et al. |
| 2013/0002253 | A1 | 1/2013 | Werner et al. |
| 2013/0127463 | A1 | 5/2013 | Matschl et al. |
| 2013/0187647 | A1 | 7/2013 | Walsh et al. |
| 2014/0152486 | A1 | 6/2014 | Apostolos et al. |

FOREIGN PATENT DOCUMENTS

| | | |
|---|---|---|
| GB | 2363845 | 1/2002 |
| KR | 10-2008-0004706 | 1/2008 |

OTHER PUBLICATIONS

Verney et al (Isotropic metamaterial electromagnetic lens, Physics Letters A 331 (2004) 244-247) (Year: 2004).*

Wiltshire et al (Microstructured Magnetic Materials for RF Flux Guides in Magnetic Resonance Imaging) Science vol. 291 Feb. 2, 2001.*

Volakis et al., Small Wideband and Conformal Metamaterial Antennas and Arrays, Dec. 8, 2010, pp. 1-48.

Erentok et al., Lumped Element Capacitor Based Two-Dimensional Efficient Metamaterial-inspired Electrically-Small Antenna, 2007, pp. 19-22.

Freire et al., "Experimental Demonstration of a µ=−1 Metamaterial Lens for Magnetic Resonance Imaging," Appl. Phy. Lett., 93, 231108 (2008).

Wiltshire et al., "Microstructured Magnetic Materials for RF Flux Guides in Magnetic Resonance Imaging," Science, 291, 849 (2001).

Freire et al., "Planar Magnetoinductive Lens for Three-Dimensional Subwavelength Imaging," Appl. Phys. Lett., 86, 182505 (2005).

Lapine et al., "Realistic Metamaterial Lenses: Limitations Imposed by Discrete Structure," Physical Review B, 82, 165124 (2010).

C.P. Scarborough, "Experimental Demonstration of an Isotropic Metamaterial Super Lens with Negative Unity Permeability at 8.5 MHz," Applied Physics Letters, 101(1), 2, (2012).

Goussetis et al., "Periodcially Loaded Dipole Array Supporting Left-Handed Propagation," IEE Proc.-Microw. Antennas Propag., vol. 152, No. 4, Aug. 2005.

Freire et al., "On the Applications of µr=−1 Metamaterial Lenses for Magnetic Resonance Imaging," Journal of Magnetic Resonance, vol. 203, 2010, pp. 81-90 (Available online:Dec. 29, 2009).

Iyer et al., "A Three-Dimensional Isotropic Transmission-line Metamaterial Topology for Free-space Excitation,"Applied Physics Letters, vol. 92, 2008, pp. 261106-1-261106-3 (Published Online: Jul. 1, 2008).

Jiang et al., "An Isotropic 8.5 MHz Magnetic Meta-Lens," 2011 IEEE International Symposium on Antennas and Propagation (APSURSI), IEEE, Jul. 3, 2011 pp. 1151-1154.

Pendry et al., "Magnetism from Conductors and Enhanced Nonlinear Phenomena," IEEE Transactions on Microwave Theory and Techniques, vol. 47, No. 11, Nov. 1999, pp. 2075-2084.

Penny et al., "Computation of Fields and SAR for MRI With Finite-Difference, Time-Domain Software," Microwave Journal, Dec. 2007 Issue.

Syms et al. "Flexible Magneto-Inductive Resonators and Waveguides," EEE Dept., Imperial College London, 2008.

Solymar et al. "Rotational Resonance of Magnetoinductive Waves: Basic Concept and Application to Nuclear Magnetic Resonance," Journal of Applied Physics, vol. 99, 2006, pp. 123908-1-123908-8.

Babu et al., "Electron Paramagnetic Study on Radical Scavenging Properties of Ceria Nanoparticles", Chemical Physics Letters, 442, 2007, pp. 405-408.

Patil et al., "Protein Adsorption and Cellular Uptake of Cerium Oxide Nanoparticles as a Function of Zeta Potential" Biomaterials 28, 2007, pp. 4600-4607.

Pendry, "Negative Refraction Makes a Perfect Lens", Physical Review Letters, vol. 85, No. 18, Oct. 30, 2000, pp. 3966-3969.

(56) References Cited

OTHER PUBLICATIONS

Tarnuzzer et al., "Vacancy Engineered Ceria Nanostructures for Protection from Radiation-Induced Cellular Damage", Nano Letters vol. 5, No. 12, pp. 2573-2577.
Zotev et al., "Microtesia MRI of the Human Brain Combined with MEG", Los Alamos National Laboratory, Applied Modern Physics Group, MS D454, pp. 1-8.
Welker et al., "Radio-Frequency Coil Selection for MR Imaging of the Brain and Skull Base," Radiology, 2001.
McDermott et al., "Microtesla MRI with a Superconducting Quantum Interference Device" PNAS May 25, 2004, vol. 101 No. 21 7857-7861.
Penciu et al., "Multi-Gap Individual and Coupled Split-Ring Resonator Structures" Optics Express, vol. 16, No. 22, Oct. 27, 2008, pp. 18131-18144.
Jelinek et al., "A Magnetic Metamaterial Composed of Randomly Oriented SRRs" Piers Online, vol. 2, No. 6, 2006, pp. 624-627.
Guven et al., Near Field Imaging in Microwave Regime Using Double Layer Split-Ring Resonator Based metamaterials, Optoelectronics Review 14:3, pp. 213-216.

* cited by examiner

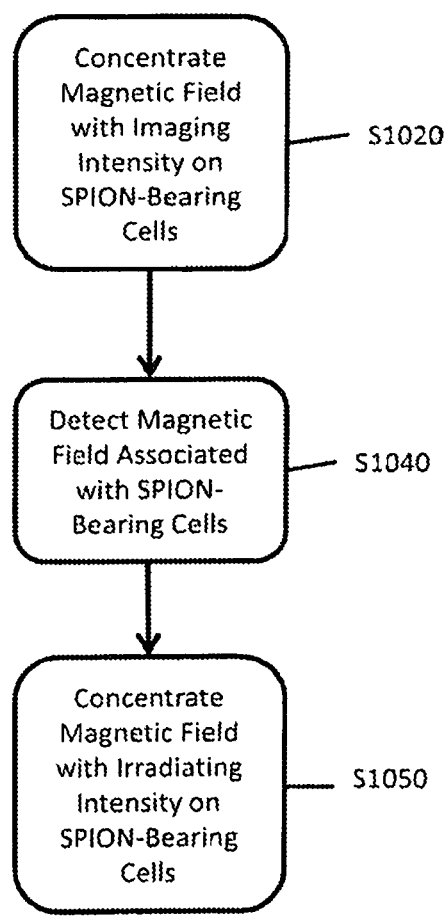

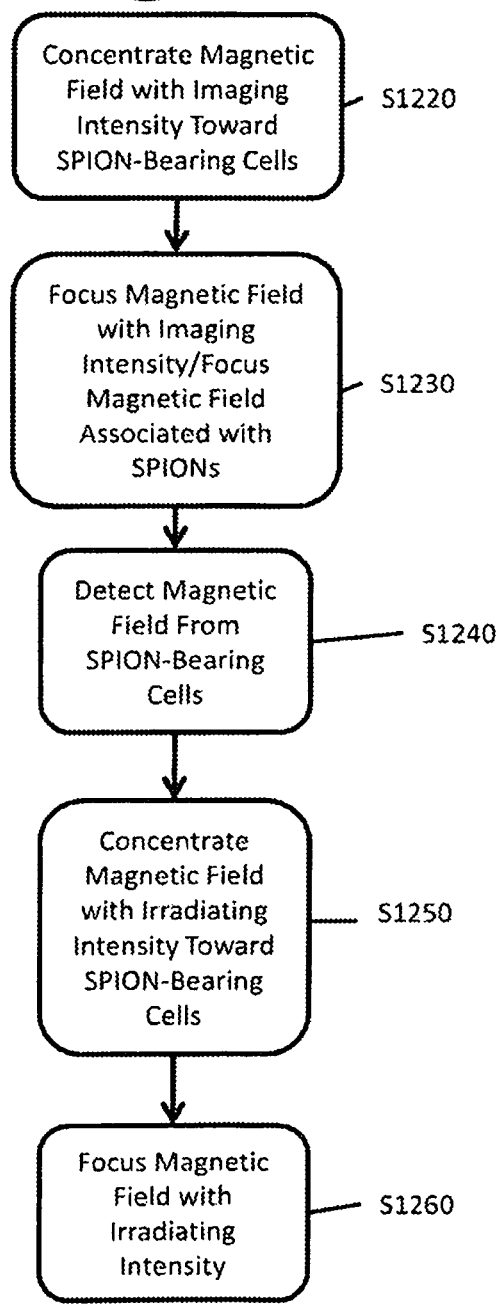

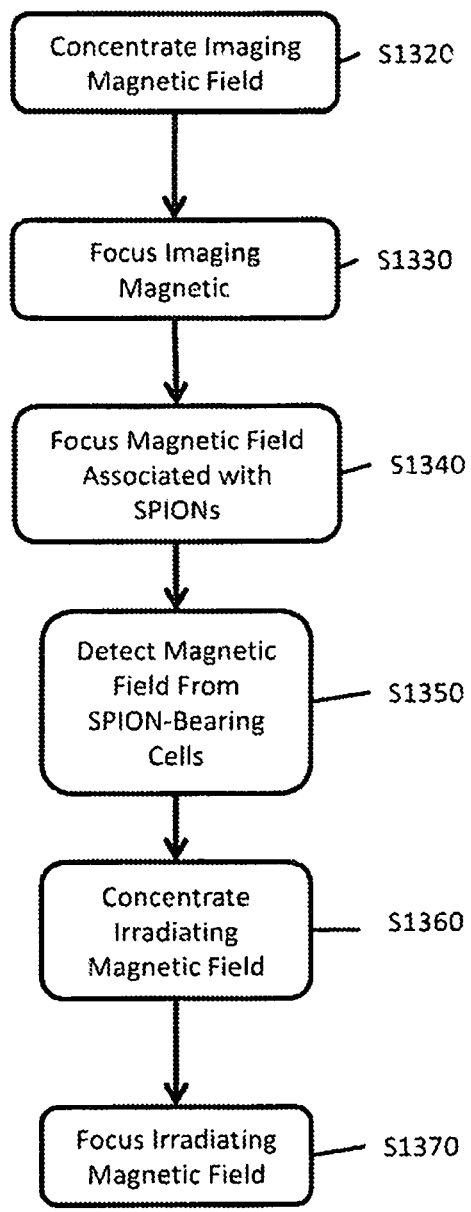

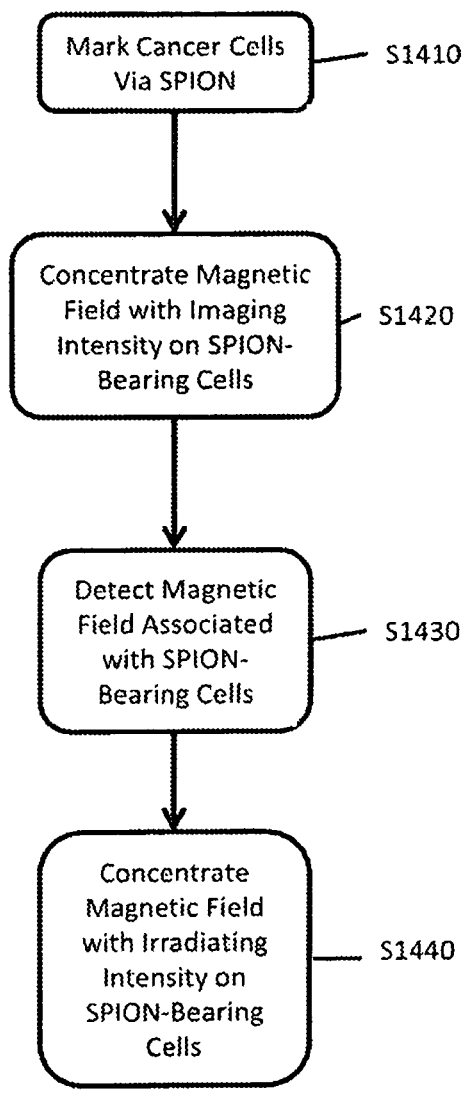

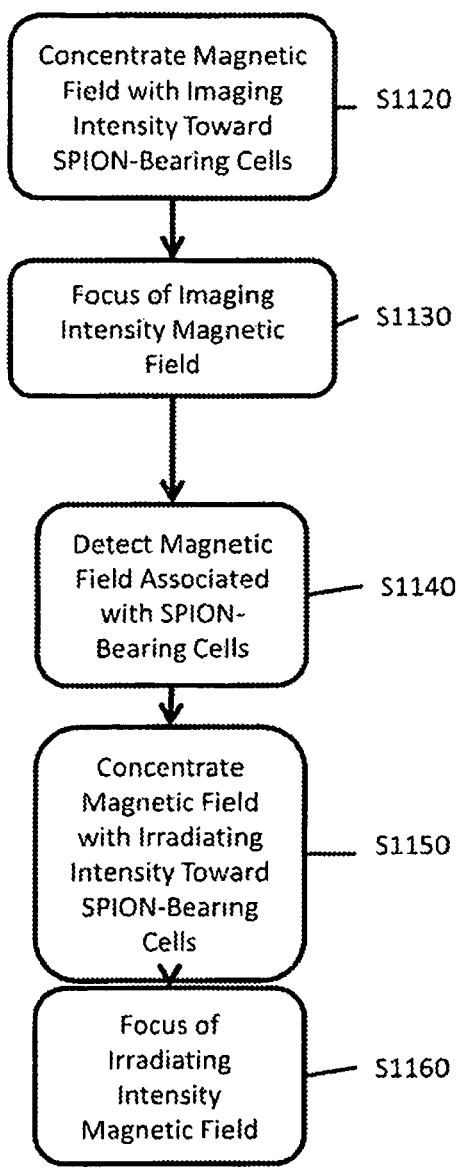

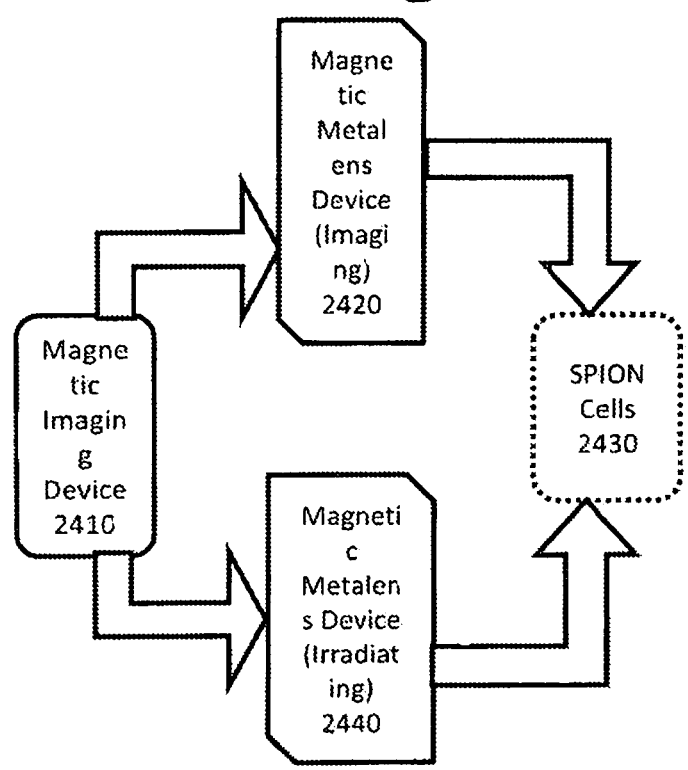

DIRECT MAGNETIC IMAGING WITH METAMATERIAL FOR FOCUSING AND THERMAL ABLATION USING SPION NANOPARTICLES FOR CANCER DIAGNOSIS AND TREATMENT

CROSS REFERENCE TO RELATED APPLICATION

This application claims priority to International Application No. PCT/US2012/043547, filed on Jun. 21, 2012, the contents of which are incorporated in full by reference herein and which claims priority to U.S. Provisional Application No. 61/499,644 filed on Jun. 21, 2011, and U.S. Provisional Application No. 61/513,903 filed Aug. 1, 2011 the contents of which are incorporated in full by reference herein.

BACKGROUND

Currently, most cancer treatment techniques involve either large doses of gamma radiation or invasive surgical techniques. Advances in magnetic imaging and in configuring magnetic particles for absorption by cancer cells, however, allow for a non-invasive alternative for imaging and treating/removing cancers and/or other malignant or diseased structures inside an organism. Such advances allow for diagnostic and treatment techniques that employ electromagnetic radiation instead of gamma radiation.

SUMMARY

Variations of techniques, systems, and devices discussed herein pertain to magnetic imaging techniques using magnetic metalenses, magnetic imaging, and magnetic induction. Techniques for performing thermal ablation inside a living organism without invasive surgical methods are also discussed.

One variation pertains to a method of identifying and destroying cancer cells bearing a plurality of surface-modified superparamagnetic iron oxide nanoparticles (SPIONs), the method comprising: imaging the SPION-bearing cancer cells with a magnetic imaging device, said imaging including generating an imaging magnetic field with the magnetic imaging device; detecting an associated magnetic field associated with the SPION-bearing cancer cells, said associated magnetic field resulting from said imaging; irradiating the detected SPION-bearing cancer cells with the magnetic imaging device, said irradiating including generating an irradiation magnetic field with the magnetic imaging device such that the SPIONs in said. SPION-bearing cells are heated as a result of said magnetic field, thereby killing the SPION-bearing cells.

In some variations, the step of irradiating including irradiating SPION-bearing cancer cells with the magnetic field at 500 kHz with an amplitude of up to 10 kA/m.

In some variations, the method also includes first focusing a magnetic field generated by the magnetic imaging device via a first magnetic metalens device. In other variations, the method also includes marking the cancer cells with said SPIONs, where said SPIONs are configured for absorption by the cancer cells, said marking creating SPION-bearing cells.

In some variations, the SPIONs are heated to a temperature of at least 43 degrees Celsius. In other variations, the magnetic imaging device is a magnetic resonance imaging device (MRI).

In some variations, the magnetic metalens device includes an isotropic metalens, and a matched resonant coil operating in conjunction with the isotropic metalens, and where the attached resonant coil is matched by equipping the coil with a matching network that includes at least a series capacitor.

In some variations, first focusing includes focusing the imaging magnetic field during said imaging. In other variations, first focusing includes focusing the irradiation magnetic field during said irradiating. In yet other variations, the method also includes second focusing with the first magnetic metalens device, where said second focusing includes focusing the associated magnetic field during said detecting. In still further variations, the method also includes third focusing with a second magnetic metalens device, where said third focusing includes focusing the irradiation magnetic field during said irradiating. In further variations still, the method also includes second focusing, with a second magnetic metalens device, where said second focusing includes focusing the associated magnetic field during said detecting.

Another variation pertains to an apparatus for non-surgical thermal ablation treatment, comprising: a magnetic imaging device that generates an imaging magnetic field for imaging cells that have absorbed superparamagnetic iron oxide nanoparticles (SPIONs); such that an associated magnetic field associated with the SPION-bearing cells is detected by a magnetic, field detector, and generates an irradiating magnetic field for irradiating the SPION-bearing cells, such that the SPIONs are heated as a result of the magnetic field generated by the magnetic imaging device, thereby killing the SPION-bearing cells.

In some variations, the apparatus also includes a plurality of surface-modified SPIONs configured for absorption by cells of an organism, said SPIONs being administered to the organism to create said SPION-bearing cells.

In some variations, the apparatus also includes a first magnetic metalens device, where said first magnetic metalens device focuses a magnetic field generated by the magnetic imaging device. In further variations, the first magnetic metalens device includes: an isotropic metalens, and a matched resonant coil operating in conjunction with the metalens, said coil being equipped with a matching network that includes at least a series capacitor.

In some variations, the apparatus also includes another magnetic metalens device, where the first magnetic metalens device focuses the imaging magnetic field, and the additional magnetic metalens device focuses the irradiating magnetic field. In other variations, the first magnetic metalens device focuses said associated magnetic field for detection by the magnetic field detector.

In some variations, the apparatus may, include another magnetic metalens device, where the first magnetic metalens device focuses the imaging magnetic field, and the additional magnetic metalens device focuses the associated magnetic field for detection by the magnetic field detector. In further variations, the isotropic metalens includes a periodic array of subwavelength cubic unit cells, and where each cubic unit cell includes a conducting loop and capacitor on each of six inner faces of the cell. In yet further variations, the matching network further includes a tapered microstrip that transforms an impedance of the resonant coil.

In some variations, the matched resonant coil is a receiving coil. In other variations, the matched resonant coil is a transmitting coil. In yet other variations, the magnetic metalens device includes a second matched resonant coil, where the matched resonant coil is a transmitting coil and the second matched resonant coil is a receiving coil.

In some variations, the irradiating magnetic field is administered at 500 kHz and has an amplitude of up to 10 kA/m. In other variations, the magnetic imaging device is a magnetic resonance imaging device (MRI).

In some variations, the SPIONs are configured to have the same diameter. In other variations, the SPIONs comprise iron oxide nanoparticles having a large magnetic moment. In yet further variations, the apparatus may also include the magnetic field detector, said magnetic field detector being configured to detect said associated magnetic field.

Another variation pertains to a magnetic metalens device, the metalens device comprising: an isotropic metalens; a matched resonant coil operating in conjunction with the isotropic metalens; and a matching network that includes at least a series capacitor, where the matched resonant coil is equipped with said matching network.

In some variations, the isotropic metalens includes a periodic array of subwavelength cubic unit cells, each cubic unit cell including a conducting loop and capacitor on each of six inner fates. In some variations, the matched resonant coil is a receiving coil. In some variations, the matched resonant coil is a transmitting coil. In other variations, the magnetic metalens device includes a second matched resonant coil, where the matched resonant coil is a transmitting coil and the second matched resonant coil is a receiving coil. In some variations, the magnetic metalens device has a magnetic permeability ($\mu$) of −1. In further variations, the matching network includes a tapered microstrip that transforms an impedance of the matched resonant coil.

Another variation pertains to an imaging device, said imaging device comprising a magnetic field generating device that generates magnetic field for imaging to be directed at cells in an organism; a first magnetic metalens device that focuses the magnetic field for imaging; superparamagnetic iron oxide nanoparticles (SPIONs), which are absorbed by said cells; and a magnetic field detector that detects a magnetic field associated with SPION-bearing cells, said associated magnetic field being caused by the focused imaging magnetic field.

In some variations, a magnetic metalens device includes an isotropic metalens, and a matched resonant coil operating in conjunction with the metalens, where the coil is equipped with a matching network that includes at least a series capacitor. In some variations, a magnetic metalens device also focuses said associated magnetic field for detection. In further variations, another magnetic metalens device focuses the magnetic field associated with said SPION-bearing cancer cells.

In some variations, the magnetic field generating device, further concentrates a magnetic field for irradiating the SPION-bearing cancer cells such that the SPIONs are heated a result of the magnetic field for irradiating, thereby killing the SPION-bearing cells. In further variations, the SPIONs are heated to a temperature of at least 43 degrees C.

Another variation pertains to a cancer treatment device, the device comprising; a magnetic field generating device that concentrates a magnetic field for irradiating to be directed at cancer cells, superparamagnetic iron oxide nanoparticles (SPIONs), which are absorbed by the cancer cells to create SPION-bearing cancer cells; where the SPION-bearing cancer cells are heated to a temperature of at least 43 degrees C. as a result of the magnetic field for irradiating, thereby killing the SPION-bearing cancer cells.

Some variations also include a magnetic metalens device which focuses the magnetic field for irradiating to be directed at SPION-bearing cancer cells. In some variations, the metalens device includes an isotropic metalens, and a matched resonant coil operating in conjunction with the metalens, where the coil is equipped with a matching network that includes at least a series capacitor.

Another variation pertains to a cancer treatment method, the method comprising: generating a magnetic field for irradiating to be directed at cancer cells bearing a plurality of surface-modified superparamagnetic iron oxide nanoparticles (SPIONs) with a magnetic imaging device; focusing the generated magnetic field via a magnetic metalens device; and irradiating the SPION-bearing cancer cells with the focused magnetic field such that the SPIONs are heated a result of the focused magnetic field.

In some variations, the SPIONs are heated to a temperature of at least 43 degrees C., thereby killing the SPION-bearing cancer cells.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The present invention will become more fully understood from the detailed description given herein below and the accompanying drawings which are given by way of illustration only, and thus are not limitative of the present invention, and wherein FIG. 1 is a block diagram of an embodiment of a method as described herein;

FIG. 1a is a block diagram of an embodiment of a method as described herein;

FIG. 1b is a block-diagram of an embodiment of a method as described herein;

FIG. 1c is a block diagram of an embodiment of a method as described herein;

FIG. 1d is a block diagram of an embodiment of a method as described herein;

DETAILED DESCRIPTION

Figure 2A:
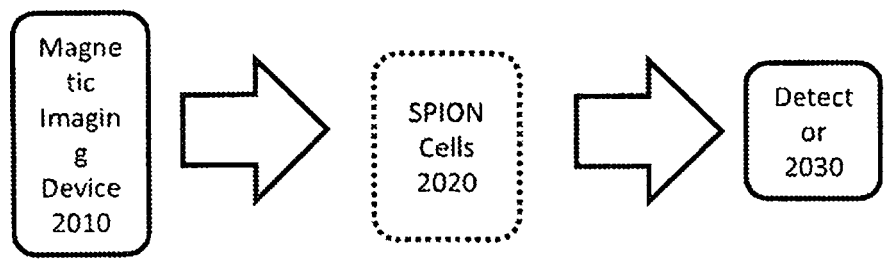
FIG. 2a is a block diagram of an embodiment of an apparatus as described herein.

The following detailed description of the techniques and solutions discussed herein refers to the accompanying, drawings. The same reference numbers in different drawings identify the same or similar elements. Also, the following detailed description does not limit the techniques and solutions disclosed herein. Instead, the scope of the techniques and solutions discussed herein is defined by the appended claims and equivalents thereof.

FIG. 1a depicts a block diagram of an embodiment of a method of identifying and/or destroying cancer cells using surface-modified superparamagnetic iron oxide nanoparticles (SPIONs). In the variation shown, the SPIONs may have already been administered to a patient in a manner that allowed the cancer cells to absorb the SPIONs. In S1020, the SPION-bearing cancer cells are imaged or otherwise exposed to a magnetic field generated by a magnetic imaging device or other magnetic field emission device. The intensity of the magnetic and electric fields produced is preferably limited by the values designated by the FDA, due to the ability to heat human tissue. In one variation, the magnetic imaging device is a 3 Tesla (T) magnetic resonance imaging device (MRI) operating at 127.7 MHz. Other variations may use MRIs of different intensity or having different frequency. Yet other variations may not even use an MRI and may instead use a direct magnetic imaging device such as the one described in U.S. patent application Ser. No. 12/801,799, filed on Jun. 25, 2010, the entire contents of which are hereby incorporated by reference. In a further variation, the magnetic imaging device is a surface ID imager. In yet a further variation, the magnetic energy may be provided by a magnetic source other than an imager. In some variations, controlled or tunable electromagnets not associated with imaging devices may be used to generate a field that is then detected or otherwise measured by a separate measurement device.

After the SPIONs are irradiated, a magnetic field associated with the SPION-bearing cancer cells can be detected S1040. For variations that accomplish detection with imaging techniques, the magnetic RF pulse must be disposed at 90 degrees perpendicular to the polarizing main field. The associated magnetic field can be detected through the detection of the magnetic resonance image in variations that employ an MRI, or by direct detection only of changes in magnetic field intensities, detected in a similar way to diffusion tensor measurements in motion resonance, in variations that employ direct magnetic imaging devices or techniques.

After being detected, the SPION-bearing cancer cells are irradiated by a magnetic field generated by a magnetic irradiation device S1050; causing the SPION-bearing cancer cells to heat to a temperature of at least 43 degrees C. In some variations, the magnetic irradiation device may be an MRI, such as, for example, a 3T MRI machine operating a 127.7 MHz. In other variations, the magnetic irradiation device may be a direct magnetic imaging device or one or more electro-magnetics or other electro-magnetic (EM) radiation sources not otherwise used for imaging. Although the figures depict the same device being used for imaging and heating of SPIONs, other variations may employ different devices to generate imaging and heating magnetic fields.

The frequency and amplitude of the magnetic field applied to the SPIONs are dependent upon the diameter and magnetization of the SPIONs, where the diameter of the SPIONs is selected to best identify and/or destroy cancer cells. In one variation, irradiation of the SPION-bearing cancer cells occurs with a magnetic field at 500 kHz and with an amplitude of up to 10 kA/m. SPIONS of various diameter may be associated with higher or lower field frequencies or amplitudes.

In a further embodiment, as described in FIG. 1d, a variation of a method of identifying and destroying cancer cells using SPIONs may also include the process of marking the cancer cells with SPIONs S1410, which have been configured to be absorbed by the cancer cells 16 one variation, such a marking process may be realized by oral administration of the SPIONs into a subject's body, after which the SPIONs are absorbed by the cancer tells. In another variation, such a marking process may be realized by administration through injection of the SPIONs into a subject's body, after which the SPIONs are absorbed by the cancer cells. In other variations the marking process may involve using SPIONs comprising iron oxide nanoparticles having a large magnetic moment. In some variations, the marking process may involve using SPIONs configured to have the same diameter. In one variation, the diameter of the SPIONs may be configured specifically to the thickness of the cancer cell area. In some such variations, a SPION diameter may be selected to best identify and destroy the cancer cells. In some variations, smaller diameter SPIONs may be preferred as larger diameters may meet with diffusion issues through larger masses. Once the SPIONs are administered to a patient or organism, they may be imaged S1420 to detect their location within the organism S1430.

In the case of cancer treatment, the steps of imaging S1420 and detection S1430 may be used to determine whether the cancer cells have absorbed a sufficient amount of SPIONs to enable the cancer cells to be killed by heating the SPIONs using an intense magnetic field S1440.

FIG. 1e depicts a block diagram showing another embodiment a method of identifying and destroying cancer cells bearing a plurality of SPIONs. In the embodiment shown, after generating a magnetic field with imaging intensity S1120; the method further includes a focusing step that focuses the magnetic field generated by the magnetic imaging device via a magnetic metalens device S1130. In some variations, the magnetic field may also be concentrated S1150 and focused with a magnetic metalens device S1160 as part of the irradiating process.

In a variation where irradiation occurs shortly after (or, in some cases, during or immediately after) imaging, the magnetic field may be focused by the magnetic metalens device S130 as part of an imaging process meant to enable and improve detection of the SPION-bearing cells S1140 to improve the effectiveness of the irradiation by indicating which cells have absorbed the SPIONs and, in some cases, how concentrated the SPIONs are within the cells. Another variation of such an imaging technique will be discussed later with respect to FIG. 3.

Returning to FIG. 1e, the focused magnetic field may also be generated by the magnetic imaging device as part of a process of irradiating the SPION-bearing cancer cells S1160. Another variation of such an irradiation technique will be discussed later with respect to FIG. 4.

In some variations, the imaging process, a variation of which includes steps S1120, S1130, and S140, may be performed independently from an irradiation process, which includes steps S105 and S1160. In some variations, the imaging process and irradiation process may be performed using separate or otherwise distinct pieces of equipment. In some variations, even if the same magnetic source is used for imaging and irradiating, a metalens used or configured for imaging may be different from a metalens used or configured for irradiating.

In one variation, the process of focusing for imaging S1130 and the process of focusing for irradiating S1160 may utilize the sane magnetic metalens device. Some variations of such a magnetic metalens device may include an isotropic metalens, and a matched resonant coil operating in conjunction with the metalens, where the coil is equipped with a matching network that includes at least a series capacitor. In such a variation, a metalens may include a periodic array of subwavelength cubic unit cells, with a conducting loop and capacitor on each of the six inner faces. In some variations, a matching network may further include a tapered microstrip that transforms an impedance of the coil. In one variation, the matched resonant coil is a receiving coil. In another variation, the resonant coil is a transmitting coil. In yet another variation, the magnetic metalens device may include a second matched coil, where one of the coils is a transmitting coil, and one of the coils is a receiving coil.

In a further variation, a tunable metalens device may be used. A tunable metalens device may include a metalens having adjustable or otherwise configurable properties, such as variable impedance. In a still further variations, two different metalens devices may be used—one for focusing during imaging and ore for focusing during irradiating. In one variation, a magnetic metalens device where µ=−1 (used for enhancing a magnetic field) may be used for imaging, while a second metalens device where n=−1 (for focusing a magnetic field) may be used for irradiating. In some such variations, the irradiating metalens is preferably tuned or otherwise configured to operate at the SPION frequency. In some variations, the irradiating metalens is preferably positioned as close to the SPION-bearing cancer cells as possible. In such variations, the irradiating metalens may be disposed In a further variation, as depicted in FIG. 1b, a focusing operation S1230 may include focusing a magnetic field associated with the SPION-bearing cancer cells that have been imaged S1220. In other words, the focusing operation may include focusing for imaging, and/or may also include a focusing operation for detection of imaging results S1230. The magnetic metalens device utilized in such post-imaging, pre-detection focusing may include a matched antenna and metalens placed in near or direct contact with the targeted area to ensure maximum efficiency. After such a post-imaging, pre-detection focusing S1230, the focused magnetic field from SPION-bearing cells may be detected S1240. After detection S1240, which may determine location and concentration of SPIONs within the SPION-bearing cells, an irradiation process may be carried out on the SPION-bearing cells. In some variations, such irradiation may include concentrating an irradiating magnetic field towards the SPION-bearing cells S1250 and focusing the concentrated field S1260 to improve the desired effects thereof. In some variations, the desired effects may include heating the SPIONs as a result of exposure to the magnetic field, such that the SPION-bearing cells are killed as a result of the heating. In yet a further variation, as depicted in FIG. 1c, after exposing the SPION-bearing cells to an imaging intensity magnetic field S1320 that is focused before imaging S1330, a variation of a post-imaging, pre-detection focusing operation, S1340, may utilize a magnetic metalens device different from the one used for the pre-imaging focusing S1330 operation. In some variations this pre-detection focusing metalens focuses the magnetic field associated with the SPION-bearing cancer cells that have been imaged to improve or otherwise enhance the detection process S1350. After detection S1350, an irradiating magnetic field may be generated/concentrated S1360 towards the SPION-bearing cells, and, in some variations, the concentrated field S1360 may also be focused S1370 to improve or otherwise enhance the irradiation process.

In some variations of post-imaging, pre-detection focusing S1340, the magnetic metalens device is tuned to the SPION frequency and is preferably as close to the SPION-bearing cancer cells as possible. Such a pre-detection focusing magnetic metalens device may include a isotropic metalens, and a matched resonant coil operating in conjunction with the metalens, where the coil is equipped with a matching network that includes at least a series capacitor. In such a variation, a metalens may include a periodic array of subwavelength cubic unit cells. A variation of a subwavelength cubic unit cell is shown in FIG. 2g. In the variation shown, each cubic unit cell may be equipped with a conducting, loop 2900 and capacitor 2910 on each of the six inner faces. In a further variation, the matching network may include a tapered microstrip as shown in FIG. 2f. The microstrip variation shown in FIG. 2f may be equipped with a wave port 2800, capacitance region 2810, resistance region 2820, and inductance region 2830. In one variation, the wave port 2800 may be a 500 wave port. In such a variation, operating at 132 MHz, a variation of the microstrip shown in FIG. 2f may have a resistance 2820 of 26.5Ω, in inductance 2830 of 122.86 nH, and a capacitance 2810 of 11.8 pF.

Microstrip variations, such as the type shown in FIG. 2f, may be configured to transform an impedance of the coil. In one variation, the matched resonant coil is a receiving coil. In another variation, the resonant coil is a transmitting coil. In yet another variation, the first magnetic metalens device includes, a second matched coil, where one of the coils is a transmitting coil, and one of the coils is a receiving coil.

FIG. 2a shows a block diagram of an embodiment of an apparatus for cancer treatment. In the embodiment shown, the apparatus includes a magnetic imaging device 2010 that generates a magnetic field for imaging cancer cells that have absorbed SPIONs 2020, such that a magnetic field associated with the SPION-bearing cancer cells 2020 is detected by a magnetic field detector 2030. Variations of the magnetic imaging device 2010, may include MRI device, magnetic imagers, and other EM radiation sources as described previously herein.

In some variations, the intensity of the magnetic field produced by the imaging device 2010 is preferably limited to the standards codified by the FDA, and is further determined based upon specific system capabilities, size of the SPIONs, proximity, and duration of the magnetic field generation. In some variations, the SPIONs, which are preferably configured for absorption by cancer cells to create SPION-bearing cancer cells 2020, may be configured to have the same diameter.

In some variations, when imaging, a magnetic RF pulse generated by the imaging device 2010 is preferably at 90 degrees perpendicular to the polarizing main field of the imaging device 2010. In another variation, the SPIONs absorbed by or otherwise present in the SPION-bearing cells 2020 may include iron oxide nanoparticles having a large magnetic moment. In one variation, the diameter of the SPIONs may be configured specifically to the thickness of the cancer cell area, where the diameter is selected to best identify and destroy the cancer cells. In some variations, smaller diameter SPIONs may be preferred as larger diameters may meet with diffusion issues through larger masses.

In some variation, the magnetic field detector 2030 may be arranged downstream from the magnetic imaging device 2010. Variations of a magnetic field detector 2030 are preferably capable of detecting a magnetic field associated with an area indicated by the SPION-bearing cells 2020. Variations of such a detector 2030 may include a solenoid, a superconducting quantum interference device (SQUID), or a solid state magnetometer. In a further variation, the magnetic imaging device 2010 may irradiate the SPION-bearing cancer cells 2020, such that the SPIONs in the cells are heated. In some irradiating variations, the SPIONs in the SPION-bearing cells 2020 are preferably heated to a temperature of at least 43 degrees C. as a result of the magnetic field generated by the magnetic imaging device 2010. At such a temperature, the SPION-bearing cells 2020 may be destroyed as a result of heating while damage to nearby, SPION-tree cells may be minimized or avoided. Furthermore, in variations using MRI or direct magnetic imaging devices as the imaging device 2010 (and, therefore the RF/EM radiation source), such heating of SPION-bearing cells 2020 may be realized without resorting to invasive techniques such as placing a probe inside a patient's body to deliver heat, radiation, or RF/EM energy. Such irradiating variations may therefore enable non-invasive ablation of cancer cells in a living organism.

In some variations, the magnetic field is administered to the SPION-bearing cells 2020 at 500 kHz and has an amplitude of up to 10 kA/m. In other variations, the frequency and amplitude of the magnetic field may vary depending on the diameter and magnetization of the SPIONs in the SPION-bearing cell 2020. The SPIONs administered to a patient and meant to be absorbed by the cancer cells to create SPION-bearing cells 2020 are preferably designated to match the cancerous area to be treated.

Figure 2B:
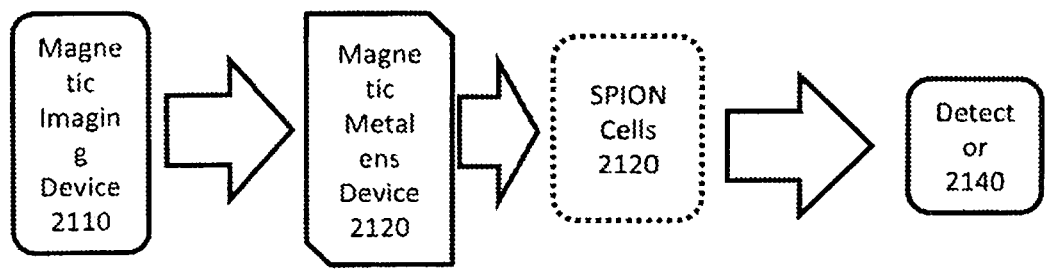
FIG. 2b is a block diagram of an embodiment of an apparatus as described herein.

In a further variation, as described in FIG. 2b, the apparatus for cancer treatment may include a magnetic metalens device 2120 to focus a magnetic field generated by a magnetic imaging device 2110 and directed at SPION-bearing cells 2120. The focused magnetic field may be detected by a magnetic field detector 2140 after the SPION-bearing cells have been imaged. Variations of a magnetic metalens device 2120 may include an isotropic metalens, and a matched resonant coil operating in conjunction with the metalens, where the coil is equipped with a matching network that includes at least a series capacitor. In some variations, the magnetic metalens 2120 may be utilized to focus the magnetic field generated by the magnetic imaging device 2110. In one variation, a magnetic metalens device 2120 having $\mu=-1$ (used for enhancing a magnetic field), may be utilized to focus the magnetic field generated by the magnetic imaging 2110 device during an imaging process. In another variation, a magnetic metalens device 2120 having n=−1 (used for enhancing a magnetic field), may be utilized to focus the magnetic field generated by the magnetic imaging device 2110 during a SPION-bearing cell 2120 irradiation process.

Figure 2C:
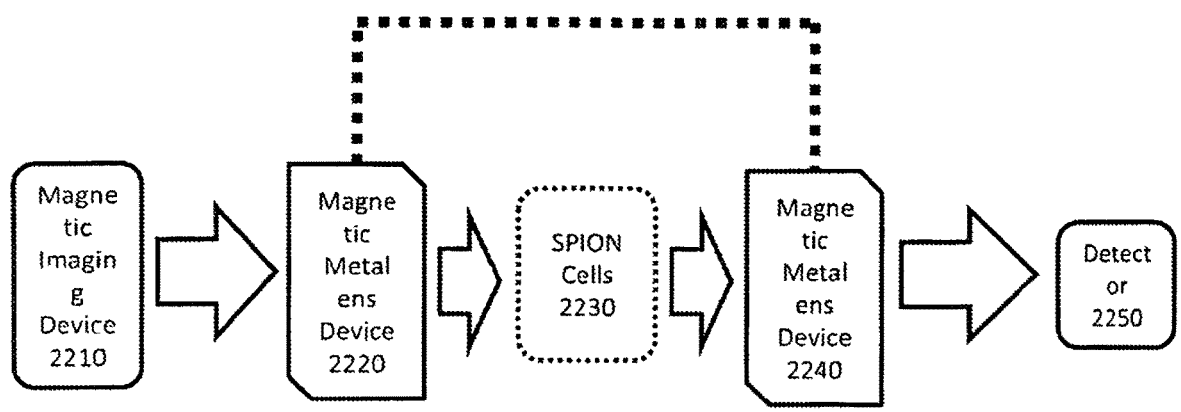
FIG. 2c is a lock diagram of an embodiment of an apparatus as described herein.

In a further variation, the magnetic metalens device 2120 may be utilized to focus the magnetic field generated by the magnetic imaging device 2110 during both imaging and irradiation processes. Such a variation is depicted in FIG. 2c. In the variation shown, a magnetic metalens device 2420 is disposed downstream of the imaging/irradiating device 2410. The metalens 2420 may be used to focus the magnetic radiation onto the SPION-bearing cells 2430 of the organism being imaged or irradiated. In an imaging variation, the magnetic radiation focused by the metalens 2420 may then be detected using a detector. In some such variations, a tunable metalens 2420, 2440 may be used. Variations of a tunable metalens may be configured with an imaging configuration 2420 for the imaging process and then configured with an irradiation configuration 2440 for a SPION irradiation process that may follow the imaging process. In such variations, both the magnetic imaging/irradiating device 2110, 2410 and the metalens device(s) 2120, 2420, 2440 may be disposed outside the body of a patient or organism undergoing cancer treatment. In some such variations, thermal ablation of cancer cells treated with SPIONs 2430, 2130 may be realized without resort to invasive surgical procedures because the magnetic radiation may be focused on and delivered to the SPIONs without having to place probes or RF sources inside a patient's body.

In another variation, also shown in FIG. 2e, a first magnetic metalens device 2420 may be utilized to focus the magnetic radiation from a magnetic imaging device 2410 during imaging of a subject organism having SPION-bearing cells 2430. A second magnetic metalens device 2440 device may then be utilized to focus the magnetic radiation generated by the magnetic imaging device 2410 during irradiation of the SPION-bearing cells 2430. Variations of an irradiation-suitable magnetic metalens device 2440 may have n=−1 and epsilon=−1. In some variations, a design of such a metalens device would involve crossed wires instead of split ring resonators. In such a variation, a metalens may include a periodic array of subwavelength cubic unit cells. A variation of such a cubic unit cell is shown in FIG. 2g and described above. In a further variation, a matching network of a matched resonant coil operating in conjunction with the metalens device(s) 2420, 2440 may further include a tapered microstrip that transforms an impedance of the coil. Variations of such a microstrip are discussed above with respect to FIG. 2f.

In one variation, the matched resonant coil is a receiving coil. In another variation, the resonant coil is a transmitting coil. In yet another variation, the imaging magnetic metalens device 2420 includes a second matched coil, where one of the coils is a transmitting coil, and one of the coils is a receiving coil.

Variations of a metalens device having transmitting and receiving coils may be configured to not only focus the magnetic radiation from the magnetic imaging device 2210, but to also focus the magnetic field signature associated with the SPION-bearing cells back to the magnetic field detector. Such a variation is depicted. In FIG. 2. In the variation shown, the positioning of the metalens device for receiving 2240 may be different than that of the metalens device for transmitting 2220. Such a positioning change may help in focusing the magnetic field signature associated with SPIONs in the SPION-bearing cells 2230 by optimizing the signal to noise ratio of the detector 2250.

Figure 2D:
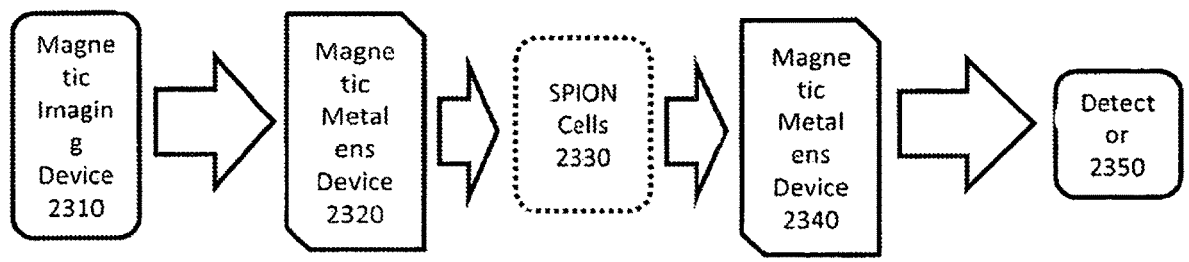
FIG. 2d is a block diagram of an embodiment of an apparatus as described herein The drawings will be described further in the course of the detailed description.
Figure 2F:
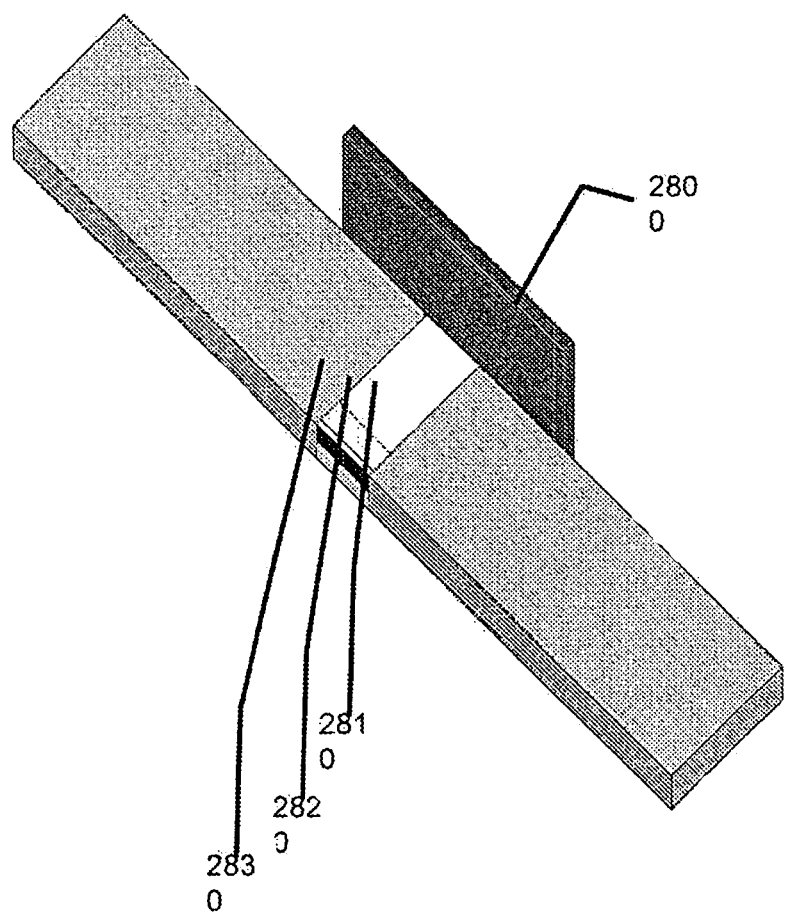
FIG. 2 is a block diagram of an embodiment of an apparatus as described herein.
Figure 2G:
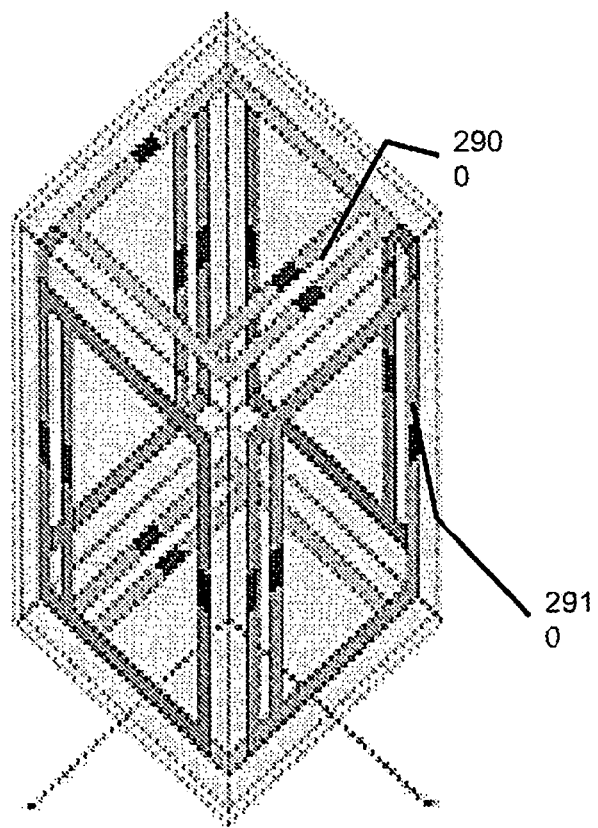

In such a variation, the magnetic metalens device for receiving 2240 is tuned to the SPION frequency and is preferably as close to the SPION-bearing cancer cells 2230 as possible. In yet another variation, as shown in FIG. 2d, a separate magnetic metalens device 2340 may focus the magnetic field signature associated with the SPION-bearing cells 2330 back to the magnetic field detector 2350. In such a variation, the imaging device 2310 and magnetic metalens device that focuses the magnetic radiation 2320 onto the SPION-bearing cells 2330 may include variations as described previously. Some variations of the imaging device 2310 may include an MRI device or a direct magnetic imaging device as discussed above. Some variations of either or both of the transmitting focusing metalens device 2320 and receiving focusing metalens device 2340 may include an isotropic metalens and a matched resonant coil operating in conjunction with the metalens. In some such variations, the coil, which may include either or both of the transmitting and receiving coils, is equipped with a matching network that includes at least a series capacitor device.

In some variations, the magnetic metalens device is tuned to the SPION frequency and is preferably as close to the SPION-bearing cancer cells as possible. In such a variation, a metalens may include a periodic array of subwavelength cubic unit cells, with a conducting loop and capacitor on each of the six inner faces. In a further variation, a matching network may further include a tapered microstrip that transforms an impedance of the coil. In one variation, the matched resonant coil is a receiving coil. In another variation, the resonant coil is a transmitting coil. In yet another variation, the magnetic metalens device includes a second matched coil, where one of the coils is a transmitting coil, and one of the coils is a receiving coil.

Some embodiments of a magnetic metalens device as depicted above may be configured for magnetic imaging and irradiating. For focusing different frequencies, the design and composition of the metalens device may be variable. Variations may occur in unit cell size, capacitors, inductors, and copper rings versus crosses. In some variations, the different components may be individually or jointly tuned to achieve a proper resonance. Also, variations in the spacing of the unit cells may affect the resonance at which the desired $\mu$ or n is achieved. In one variation, the magnetic metalens device may be configured where $\mu=-1$. In a different variation, the magnetic metalens device may be configured so that $n=-1$. In yet another variation, the metalens device may include an isotropic metalens and a matched resonant coil operating in conjunction with the metalens, where the coil is equipped with a matching network that includes at least a series capacitor. As previously explained, the composition of such a metalens device is variable based upon the frequency to be focused; therefore, the composition or configuration of the metalens device (and any associated resonant coil(s)) may be different during imaging or irradiating. Furthermore, a metalens device used or configured for focusing during a transmission portion of an imaging process may be different from a metalens device used or configured for focusing during a reception portion of an imaging process.

In further variations, the coil equipped with a matching network (connected to the transmitting antenna), and the series capacitor may also be variable to facilitate the power required for the strength of the input field. The matching network may be disposed behind the metalens (in close proximity), and may be connected to the transmitting antenna. In yet another variation, the resonant coil may be a receiving coil. In a still further variation, the resonant coil may be a transmitting coil. In one variation, the magnetic metalens device may include a second matched coil, where one of the coils is a transmitting coil and one of the coils is a receiving coil.

The invention being thus described, it will be obvious that the same may be varied in many ways. Such variations are not to be regarded as departure from the spirit and scope of the invention, and all such modifications as would be obvious to one skilled in the art are intended to be included within the scope of the following claims

We claim:

1. An apparatus for non-surgical thermal ablation treatment, comprising:
a magnetic field detector; and
a magnetic imaging device having a first magnetic metalens device tunable between an irradiating arrangement and an imaging arrangement and a second magnetic metalens device;
wherein the first magnetic metalens device comprising an isotropic metalens;
wherein the isotropic metalens comprising a periodic array of subwavelength cubic unit cells;
wherein the magnetic imaging device is configured for imaging cancer cells that have absorbed superparamagnetic iron oxide nanoparticles (SPIONs);
wherein said first magnetic metalens device is configured to focus a magnetic field, at the SPION-bearing cells, generated by the magnetic imaging device, said first magnetic metalens device comprising a matched resonant coil operating in conjunction with the metalens, said coil being equipped with a matching network that includes at least a series capacitor, and a second matched resonant coil, where the matched resonant coil is a transmitting coil and the second matched resonant coil is a receiving coil;
wherein an associated magnetic field associated with the SPION-bearing cells is configured to be detected by the magnetic field detector;
wherein the magnetic imaging device is configured to generate an irradiating magnetic field at a frequency of 500 kHz and at an amplitude of up to 10 kA/m for irradiating the SPION-bearing cells;
wherein the SPIONs are heated as a result of the magnetic field generated by the magnetic imaging device, thereby killing the SPION-bearing cells; and
wherein the first magnetic metalens device configured to focus the magnetic field generated by the magnetic imaging device during at least one of imaging and irradiation by the magnetic imaging device, and the second magnetic metalens device configured to focus the irradiating magnetic field.

2. The apparatus of claim 1, where the first magnetic metalens device focuses said associated magnetic field for detection by the magnetic field detector.

3. The apparatus of claim 1, further comprising a third magnetic metalens device, where the first magnetic metalens device focuses the imaging magnetic field, and the third magnetic metalens device focuses the associated magnetic field for detection by the magnetic field detector.

4. The apparatus of claim 1, wherein each cubic unit cell of the isotropic metalens includes a conducting loop and capacitor on each of six inner faces of the cell.

5. The apparatus of claim 1, where the matching network further includes a tapered microstrip that transforms an impedance of the resonant coil.

6. The apparatus of claim 1, where the matched resonant coil is a transmitting coil.

7. The apparatus of claim 1, further comprising a plurality of surface-modified SPIONs configured for absorption by cells of an organism, said SPIONs being administered to the organism to create said SPION-bearing cells.

8. The apparatus of claim 1, where the magnetic imaging device is a magnetic resonance imaging device (MRI).

9. The apparatus of claim 1, where the SPIONs are configured to have the same diameter.

10. The apparatus of claim 1, where the SPIONs comprise iron oxide nanoparticles having a large magnetic moment.

11. The apparatus of claim 1, wherein the magnetic metalens device is configured to have $n=-1$ for focusing the magnetic field.

12. The apparatus of claim 1, wherein a design of the magnetic metalens device involves crossed wires instead of split ring resonators.

13. The apparatus of claim 1, wherein the magnetic imaging device and the metalens device are disposed outside a body of a patient undergoing cancer treatment.

* * * * *